United States Patent [19]

Gross

[11] 3,996,344

[45] Dec. 7, 1976

[54] PHENETHYLAMINE ANTIGENIC CONJUGATES, THEIR PREPARATION, ANTIBODIES AND USE

[75] Inventor: Stanley Joseph Gross, Encino, Calif.

[73] Assignee: Biological Developments, Inc., Encino, Calif.

[22] Filed: Dec. 10, 1974

[21] Appl. No.: 531,220

Related U.S. Application Data

[63] Continuation-in-part of Ser. No. 253,632, May 15, 1972, Ser. No. 462,517, April 19, 1974, Ser. No. 160,559, July 7, 1971, and Ser. No. 480,097, June 17, 1974, said Ser. No. 253,632, is a continuation-in-part of Ser. No. 89,929, Nov. 16, 1970, abandoned, which is a continuation-in-part of Ser. No. 45,558, June 11, 1970, abandoned, said Ser. No. 462,517, is a continuation of said Ser. No. 89,929, said Ser. No. 160,559, is a continuation-in-part of said Ser. No. 89,929, said Ser. No. 480,097, is a continuation of Ser. No. 160,150, July 6, 1971, which is a continuation-in-part of said Ser. No. 89,929.

[52] U.S. Cl. ............................ 424/1.5; 260/112 R; 424/7; 424/12; 424/88
[51] Int. Cl.² ................. G01N 33/00; A61K 39/00; G21H 5/02
[58] Field of Search ................... 260/112 R, 570.8; 424/1, 1.5, 7, 12, 88

[56] References Cited

UNITED STATES PATENTS

| | | | |
|---|---|---|---|
| 3,709,868 | 1/1973 | Spector | 424/12 X |
| 3,856,469 | 12/1974 | Schneider et al. | 260/570.8 R X |
| 3,878,187 | 4/1975 | Schneider et al. | 424/12 X |
| 3,884,898 | 5/1975 | Schneider | 424/12 X |
| 3,901,654 | 8/1975 | Gross | 424/1 X |

Primary Examiner—Benjamin R. Padgett
Assistant Examiner—Christine M. Nucker
Attorney, Agent, or Firm—McAulay, Fields, Fisher & Goldstein

[57] ABSTRACT

Antigenic phenethylamine conjugates are produced by blocking the amine of the phenethylamine hapten with a group, coupling of the phenethylamine to a carrier, and removal of the blocking group. Specific phenethylamines useful in this invention are amphetamine, epinephrine, and norepinephrine. The antigens thus produced can be used to raise antibodies in animal bodies, the antibodies being specific to the phenethylamine compound employed. The antibodies are useful in assaying for the phenethylamine hapten compounds.

21 Claims, No Drawings

PHENETHYLAMINE ANTIGENIC CONJUGATES, THEIR PREPARATION, ANTIBODIES AND USE

CROSS-REFERENCES TO RELATED APPLICATIONS

This application is a continuation-in-part of my co-pending application Ser. No. 253,632, filed May 15, 1972, which was a continuation-in-part of co-pending application Ser. No. 89,929, filed Nov. 16, 1970, now abandoned, which, in turn, was a continuation-in-part of my application Ser. No. 45,558, filed June 11, 1970, now abandoned; of my co-pending application Ser. No. 462,517, filed April 19, 1974, which was a continuation of application Ser. No. 89,929, aforereferenced; of application Ser. No. 160,559, filed July 7, 1971, which was a continuation-in-part of Application 89,929, aforereferenced; and of application Ser. No. 480,097, filed June 17, 1974, which is a continuation of application Ser. No. 160,150, filed July 6, 1971, which was a continuation-in-part of Application 89,929, aforereferenced.

BACKGROUND OF THE INVENTION

1. Field of the Invention

This invention relates to immunoassaying. Immunoassayings are proving of immense value in medicine and biology for the assaying of the constituents of biological fluids, because of the sensitivity and specificity of such assaying. In immunoassaying procedures, for a given target compound, a synthetic antigen is generally first prepared. Heretofore, this has usually been accomplished by coupling the target compound, through a coupling group to a carrier which confers antigenicity to the entire compound. The compound coupled to the carrier is usually known as a hapten and, when coupled, it exhibits antigenic determinacy by causing the antibodies produced to be specific to it. Thus, the antibodies produced have a distinct and unique character, such that they will bind with only a specific compound or class of compounds. The objective in devising the synthetic antigen-hapten conjugate is to provide a compound which will generate antibodies that are specific to the target compound.

Antibodies are prepared by injecting the synthetic hapten-antigen conjugate into competent vertebrate animals and recovering blood serum from the animals after they have had time to generate antibodies. Typical and preferred animals are mammals, e.g., rabbits and goats.

The principal problem is usually synthesizing antigens that are sufficiently specific. Biological fluids such as blood and urine frequently contain very closely related compounds and it is common for antibodies to be unable to distinguish the target compound from close relatives, or sometimes even distant ones. The antibody is then considered to be a poor one and is said to have low specificity and high cross-reactivity.

The assay itself is commonly a competitive binding assay. In such an assay, the target compound, which is not necessarily extracted, is allowed to compete with known quantities of a radiation labeled standard to bind with a known quantity of a specific antibody. From measurement of the proportion of the labeling in the standard-antibody complex that results, the amount of target compound present can be calculated. Radioactive labeling is particularly convenient. Fluorescent perturbation can be used. Normally it will be necessary to remove any unreacted labeled standard, before making the determination on the antibody complex.

2. The Prior Art

The cross-referenced applications disclosed, inter alia, hapten-antigen conjugates in which a hapten is coupled to an antigen through a diazo group, a phenyl ring, and an amide bond to a proteinic antigen. Numerous haptens are disclosed, and steroids are of particular interest.

A synthesis is described in which the hapten is coupled to the amine of an aminoaryloic acid by diazotization, and the product is then coupled to an antigenic protein with an amide bond.

Other proposals for the preparation of phenethylamine conjugates have involved coupling through a functional group, such as the amine, which is undesirable.

Spector in U.S. Pat. No. 3,704,282 discloses the preparation of catecholamine antigens by carbodiimide condensation of the amine with the carboxyl group of an immunogenic material, such as a protein or polypeptide. Included within the generic definition of catecholamine are hydroxyphenethylamines, and these include norepinephrine, the latter being one of the materials of spacific interest according to the present application. The antigens reported in Spector are said to be useful for raising antibodies, and radiation-labeled competition assays are described. Apparently, according to the Spector disclosure, antibody binding with norepinephrine was obtained, and there is a report of an in vitro study of its characteristics. However, Spector gives no cross-reactivity data, and there is no evidence indicating that the antibody generated according to Spector would be useful in assays as there is nothing to indicate the specificity or the binding affinity of the antibody.

In U.S. Pat. Nos. 2,372,066 and 2,301,532, Fell, a number of methods are disclosed for coupling of histamine, an organic ring compound with a primary amine group, to a protein for the purpose of preparing an antigenic conjugate. The objective of these patents is to produce an in vivo response, and there appears to be no consideration of the use of the antibodies in vitro. Many reaction sequences are shown, though most involve the coupling of the protein through the primary amino group. Though there are a few examples which involve coupling through the histidyl ring, the preferred route is that of Examples 1 through 4 of U.S. Pat. No. 2,372,066, the materials produced by that route reportedly producing an antigen in which the histamine is coupled to the protein through an amide bond derived, in part, from the histamine amino group, through a phenyl ring which, in turn, is coupled through a diazo group to the protein. However, histamine is not a phenethylamine, and neither of these patents suggests the coupling of phenethylamine through the ring for use in production of antigens, for subsequent production of antibodies from these antigens, and the use of the resulting antibodies with low cross-reactivity in assays for target compounds.

In "Peptides and Amino Acids," Kopple (W. A. Benjamin, Inc., 1966), pages 36 through 38, the use of blocking groups in peptide synthesis is disclosed. The use of trifluoroacetyl as an amine blocking group is specifically mentioned. However, there is no consideration of antigen synthesis or of its problems, and the teaching regarding the stability of the trifluoroacetamide suggests this to be an unsuitable blocking group in at least some of the reactions of particular interest here.

BRIEF DESCRIPTION OF THE INVENTION

This invention relates to a phenethylamine antigen which is the reaction product of a blocked phenethylamine hapten and an antigenicity-conferring carrier where coupling has been carried out through a derivative formed at an unsubstituted ring atom of the phenethylamine hapten. This invention further relates to antibodies produced from the antigens.

The hapten compounds from which antigens are to be made, according to the present invention have the formula:

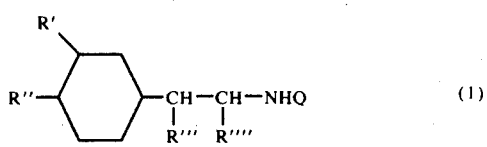

(1)

where R' and R" are individually selected from the class consisting of —H, —OH, and —OCH₃, where when either R' or R" is —OCH₃, the other is —OH; R''' is selected from the class consisting of —H and —OH; R'''' is selected from the class consisting of —H, —CH₃, and —C₂H₅; and Q is selected from the class consisting of —H and —CH₃. The haptenic materials which are of particular interest are amphetamine of formula:

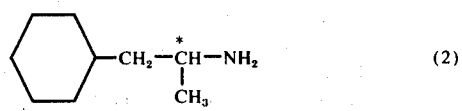

(2)

where R', R", R''' and Q are —H, and R'''' is —CH₃; norepinephrine of formula:

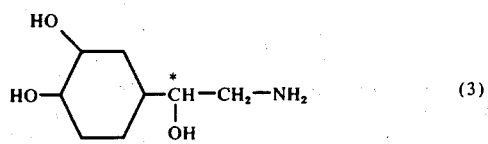

(3)

where R', R", and R''' are —OH, and R'''' and Q are —H; and epinephrine of formula:

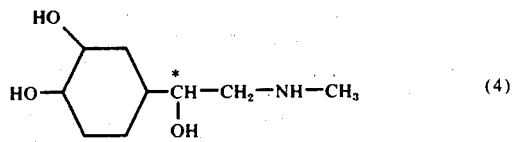

(4)

where R', R", and R''' are —OH, R'''' is —H, and Q is —CH₃. Each of the compounds of particular interest is optically active, the asymetric carbon atom being indicated by the asterisk. Generally, it will be preferred to use an active isomer for antibody specificity to the commonly used forms that are also usually optically active.

The antigens of the present invention are prepared according to a process comprising the steps of:

(1) reacting a phenethylamine at the amine with a blocking agent to form an amine-blocked phenethylamine;

(2) derivatizing the phenyl ring of the amine-blocked phenethylamine;

(3) coupling the phenethylamine to a carrier through the group derivatized into the ring in step 2; and (4) removing the blocking group and reforming the amine to yield phenethylamine conjugated to the carrier through the ring derivative. These steps need not necessarily be carried out in the sequence shown. For example, steps 2 and 3 can be reversed in the sense that the group to be derivatized is first coupled to the carrier and then the conjugate is derivatized into the phenethylamine.

In order to be capable of conferring antigenicity, the carrier will normally be antigenic itself, although it may be incomplete antigen, becoming complete only when coupled to the hapten. To be antigenic, the carrier must be an immunogenic substance, that term being used to refer to a substance capable of eliciting production of antibodies in a host animal to which the immunogenic substance is administered. While, in general, it is believed that the terms "carrier" and "immunogenic substances" are clearly understood in the art, and the discussion herein is not meant to modify the ordinary significance of the terms, further definition is provided here for a clearer understanding of the development.

The animal to which the antigenic substance is administered must be one having an effective immunological system. The immunogenic substances must be "foreign" to the animal, in the sense of not being "self." That is, the immunogenic substance administered must not be one which is a natural body substance of the animal and would, therefore, be accordingly tolerated by the animal's immunological system.

Generally, the antibodies elicited upon injection of the immunogenic substance into the animal will be generated by the host animal and will be capable of reacting or binding with the antigen in an observable and selective way. Thus, the antibodies will display some degree of discrimination between the administered immunogenic substance and other immunogenic materials.

The requirements for immunogenicity are not fully understood. However, it appears that for a molecule to be antigenic, it must have a certain complexity and a certain minimal molecular weight. Formerly, it was thought that the lower molecular weight limit to confer antigenicity was about 5,000. However, antigenicity has recently been demonstrated with molecules having molecular weights as low as 2,000. Molecular weights of 3,000 and more appear to be more realistic as a lower limit for immunogenicity, and approximately 6,000 or more is preferred.

Exemplary immunogenic carrier materials are those set forth in Cremer et al., "Methods in Immunology," (1963), W. A. Benjamin Inc., New York, pages 65 to 113. That disclosure is herein incorporated by reference. The carrier material can be a natural or synthetic substance, provided that it is an antigen or a partial antigen. For example, the carrier material can be a protein, a glycoprotein, a nucleoprotein, a polypeptide, a polysaccharide, a lipopolysaccharide, or a polyaminoacid. An example of an apparently incomplete antigen is the polypeptide, glucagon.

A preferred class of natural carrier materials is the proteins. Proteins can be expected to have a molecular weight in excess of 5,000, commonly in the range of from 34,000 to 5,000,000. Specific examples of such natural proteins are bovine serum albumin (BSA), keyhole limpet hemocyanin (KLH), human immunogammaglobulin (HGG), and thyroglobulin.

Exemplary of the synthetic carrier is a polyaminoacid, polylysine. Where the synthetic antigen comprises a partially antigenic carrier conjugated with a hapten, it will generally be desirable for the conjugate to have a molecular weight in excess of 6,000, although somewhat lower molecular weights may be useful.

Preferably, the natural carrier has some solubility in water or aqueous alcohol. Also preferably, the synthetic antigen is water soluble. Desirably, the carriers are nontoxic to the animals to be used for generating antibodies.

The carrier must have a, or preferably a plurality of, functional moieties by means of which it can be coupled. Of course, these groups can be introduced synthetically. Preferably, in practicing the present invention, a single carrier moiety should have a plurality of hapten moieties coupled to it, for example, from about 10 to about 70. In general, the maximum possible number of haptenic moieties per carrier molecule is preferred. Subject to steric hindrance, the maximum number will be determined by the number of reactive coupling groups on the carrier. For example, with BSA, it appears that the maximum number of haptenic moieties that can be coupled is between 60 and 70.

The coupling mechanism will depend upon the particular derivative inserted in the phenyl ring and what reactive groups are available on the carrier. Any mechanism can be used to bond the phenethylamine derivative to the carrier provided that it does not modify the antigenic determinant groups of the phenethylamine, notably hydroxyl groups if present, nor introduce antigenic determinant groups that reduce the specificity of antibody raised by the synthetic antigen. A convenient mechanism, especially with a natural protein carrier, is to introduce a diazo bridge between the phenyl ring and the protein. For this an amino is introduced into the phenyl, for example by nitration and reduction. The amino group can then be diazotized and coupled to the carrier. Natural proteins frequently have aryl groups with diazotizable carbons that provide convenient coupling points.

Alternatively, again advantageously with a proteinic carrier, the coupling may be by way of an amide bond.

The blocking agent must provide a blocking group that is bonded throughout the derivatizing and coupling reactions but is capable of being removed subsequently under conditions that do not destroy any of the bonds coupling the phenethylamine to the carrier. It is desirable for the blocking group to reduce or nugate the basic character of the amine group. An example of a useful blocking group is a fully fluorinated alkyl carbonyl, particularly trifluoroacetyl, $CF_3CO-$. When substituted in the amine, $CF_3CONH-$, the carbonyl effectively nugates the basic character of the amine and the fluorine atoms provide an electron sink that renders the group stable under extremely acid conditions. Under moderately alkaline conditons, it is unstable, however, and at room temperature (25° C.), the amine is slowly reformed when the pH is greater than about 10. Since the protein-coupling amide bond is stable up to about pH 12 (25° C.), such a blocking group can readily be removed from an amine-blocked phenethylamine protein conjugate, without destroying the conjugate, by careful control of the pH to be between 10 and 12, and preferably near 11.

The blocking agent will simply be a compound capable of being reacted with the phenethylamine to substitute the desired blocking group into the amine. Examples of reagents for introducing a trifluoroacetyl block are trifluoroacetic anhydride, ethylthioltrifluoroacetate and trichlorotrifluoroacetone. Other blocking agents include, for epinephrine and norepinephrine, in addition to other phenethylamines having hydroxyl groups in the aromatic ring, t-butoxycarbonyl which is obtained from the chloride or the oxychloride, t-amyloxy carbonyl chloride, and benzoyloxy carbonyl chlorides.

In any event, it is important that the blocking agent employed, prior to coupling of the hapten to the carrier, be one which can be easily removed to regenerate the desired antigenic material.

DESCRIPTION OF THE PREFERRED EMBODIMENTS

The present invention relates to antigenic materials of formula:

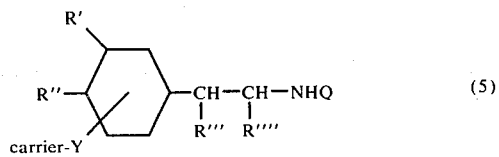

where $R'$, $R''$, $R'''$, $R''''$, and Q are as previously defined, Y is a linking group which is the residue from the reaction of a coupling agent with a reactive group derivatized into the phenyl ring at an unsubstituted carbon and of the coupling agent with the carrier, being substantially free of antigen determinacy; and the carrier is a macromolecule conferring antigenicity. In addition, the invention contemplates antibodies specific to the antigens of the invention and to a process for producing these antigens.

Thus, in the antigens of the present invention, the hapten from which the antigen is made has all of its functional groups free to exert their antigenic determinacy. This is in contrast to the general practice of the art which employs the chemically easier, or more obvious but immunologically less satisfactory approach, of coupling through the functional groups. The antibodies produced according to the present invention show good specificity and, in particular, are expected to distinguish a methyl substituent at the nitrogen atom, whereas the antigens formed by coupling through that nitrogen are not expected to produce antibodies which will accomplish that result. This is of great clinical importance in view of the different activities of epinephrine and norepinephrine, and in order to distinguish between amphetamine and methedrine. The antigens produced according to the processes of the prior art would not suggest the production of such specific antibodies.

Several sequences are possible for preparation of the antigenic materials of the present invention. These will be described below and, in the following description, the principal, exemplary blocking agent referred to will be trifluoroacetic anhydride and the trifluoroacetyl group will be denoted as TFA, it being understood that the invention includes the specific use of other blocking agents meeting the foregoing criteria. The invention contemplates three specific reaction sequences as exemplary of its broad teaching. The sequences will be described below:

Reaction Sequence A

This sequence comprises the following steps:

(1) blocking the amine of a phenethylamine by reaction with a TFA blocking agent;

(2) nitration of the phenyl ring at a point meta or para to the amine substituent referred to in paragraph (1) on an unhydroxylated phenyl carbon;

(3) reduction of the introduced nitro groups to the amine;

(4) diazotization of the amine;

(5) coupling of the diazonium-phenethylamine-TFA to a carrier; and (6) removal of the TFA block with reformation of the amine to yield the carrier-diazophenethylamine synthetic antigen conjugate.

Graphically, this sequence may be depicted as follows:

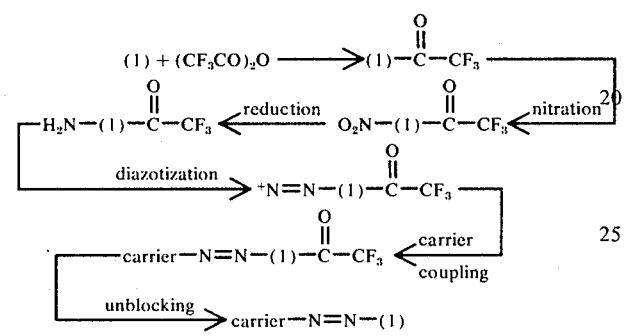

Preferably, the carrier is a natural protein, and the coupling is into a pendant aromatic ring on the protein which may, for example, be BSA. Other useful proteins for use in this reaction sequence, and to form the novel products of the present invention, are set forth in the aforereferenced co-pending applications. Many natural proteins have aromatic groups distributed on their molecules. Other antigenic or partially antigenic molecules having accessible, diazotizable aromatic rings can be used in this sequence, or alternatively other coupling means can be used.

As the foregoing structural formulae show, this sequence is preferred for phenethylamines in which the phenyl ring is unsubstituted, i.e., R' and R'' are —H rather than —OH. A reason for this is that Reaction Sequence C, to be described, is preferred for the phenols, and also there is a possibility of hydroxyls interfering with or confusing the diazotization reaction.

Aliphatic hydroxyls are tolerable in this reaction sequence since if R''' or R'''' is hydroxyl, it will be blocked by TFA. In such a case, a higher proportion of TFA will be needed.

In this sequence, it is necessary for the blocking group bond to be stable under the fiercely acidic conditions of nitration and diazotization, while also protecting the amine group. The use of TFA fulfills these conditions well.

Reaction Sequence B

This sequence comprises the following steps:

(1) blocking the amine with TFA as in Sequence A;

(2) acylating the phenyl ring using a dicarboxylic acid anhydride in a Friedel-Crafts reaction at a point meta or para to the blocked amine on an unhydroxylated phenyl carbon atom;

(3) coupling to the carrier through the carboxyl group so formed;

(4) unblocking and reforming as in A.

This reaction sequence may be depicted graphically, as follows:

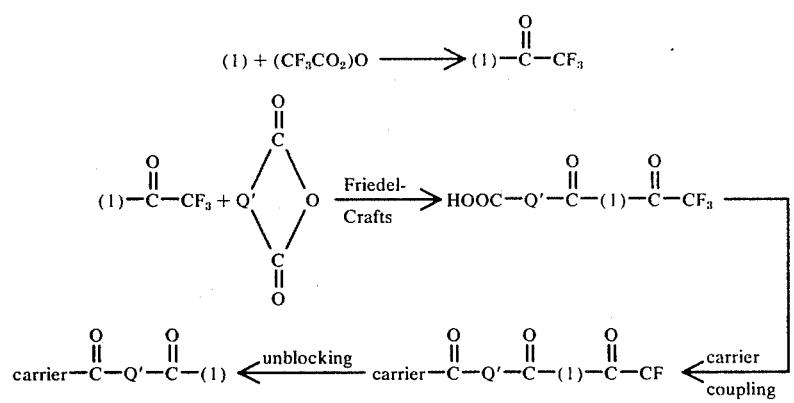

where Q' is an alkylene chain having up to 20 carbon atoms.

The carrier is preferably a protein, natural or synthetic, and the coupling preferably is effected to a protein amine group using a carbodiimide coupling agent, and is thus an amide bond. This sequence can be used with any one of the defined phenethylamines, including those with hydroxyls at R' or R'', in which case the anhydride will substitute in meta to the ethylamine position. If R' and R'' are both —H, the substitution position will be para. Thus, with succinic anhydride, the novel synthetic antigen produced will have the formula:

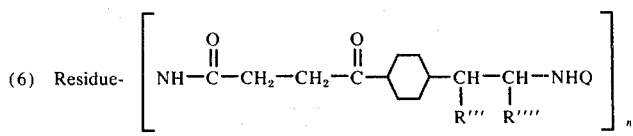

where R''', R'''', and Q are as previously defined, and $n$ is an integer of from 1 to the number of available coupling groups on the carrier. A specific example of a possible residue in formula (6) is BSA.

Reaction Sequence C

This sequence is primarily employed for phenols and comprises, following blocking of the phenethylamine:

(1) diazotization of a primary aromatic amine into the phenyl ring;

(2) coupling into a carrier;

(3) unblocking the conjugate and reforming the amine.

Alternatively, the step of coupling to a carrier can be carried out first, providing that the amine is kept available, and the complex can be diazotized into the phenyl ring of the blocked phenethylamine.

The main reaction sequence can be depicted as follows:

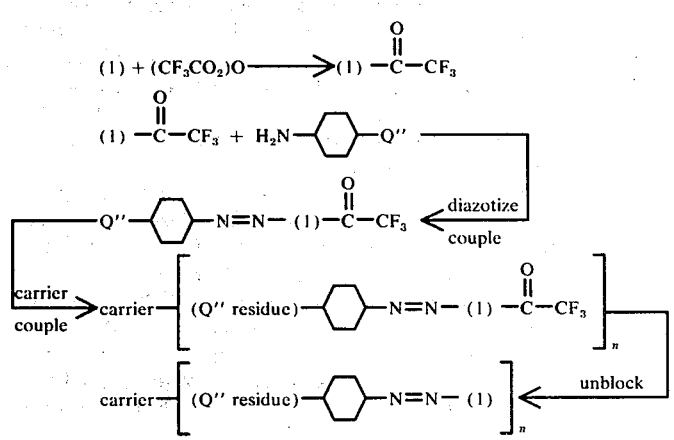

where Q" includes a reactive group that may be coupled to a reactive group on the carrier, its residue being essentially non-reactive in this sequence, and being bonded to its accompanying aryl at any position, with one or more bonds provided that the amino group is available for diazotization. For example, Q" may be a further phenyl ring conjugated to the first, but it is contemplated that not more than four such rings would be useful and, further, that not more than 20 carbon atoms in an aliphatic chain would be useful. In Reaction Sequence C, Y of formula (5) can be Q"-phenyldiazo. The reactive group on Q" may, conveniently, be a carboxyl group.

The phenethylamine can have a hydroxyl in the R" position. Of the defined alternative for R' and R" (—H and —OH), one or both must be hydroxyl to direct the diazo link to a neighboring carbon atom. Thus, the particular sequence depicted is exemplary in this respect. If R' is hydroxyl and R" is not, the diazo couple will be oriented para to the blocked ethylamine; otherwise it will be meta.

With a proteinic carrier, as an example, it is convenient for the reactive group of Q" to be a carboxyl, so that an amide bond to the carrier can be made using an available amine on the carrier. In this case a coupling agent will usually be needed to form the amide bond, an example of which is a carbodiimide. In one specific example, Q" is a carboxyl group, simpliciter so that the primary reactant in this sequence is para-aminobenzoic acid (PABA).

In general, sequences A and C are preferred to sequence B because the Friedel-Crafts reaction of sequence B gives somewhat poor yields. Sequence C is particularly preferred for phenethylamines having an aromatic hydroxyl group because of its simplicity. Sequence A will normally be preferred where R' and R" are both hydrogen. Sequence C is thus useful for the preparation of antigenic conjugates for epinephrine and norepinephrine.

In sequence C, coupling of the diazo group into the phenyl (of the blocked ethylamine) is usually carried out at a moderately alkaline pH, e.g. 9–11, which is close to the pH at which the TFA bond is destroyed. However, the diazo-coupling reaction proceeds rapidly in comparison, and can usually be effected before substantial breaking of the TFA bond occurs.

Some data suggest that an amphetamine-specific synthetic antigenic conjugate having a diazo couple into the phenyl ring (Reaction Sequence A) may generate more specific antibodies than the equivalent succinyl-coupled antigen (Reaction Sequence B). Some practical details of conditions that can be used for practicing the several reaction sequences discussed above will now be considered.

In general, it is desirable to ensure that reagents of good purity are used, and this includes the carrier material. To ensure the purity and unique character of the antigen, intermediate purification steps may be desirable.

Exemplary Conditions for Reaction Sequence A.

Blocking.

In this step a blocking agent which desirably contains the TFA (trifluoroacetyl) group is reacted with a phenethylamine.

The reaction is preferably carried out in the liquid phase using from 1 to 50 percent, by weight, of phenethylamine in an organic solvent. The solvent should not have hydroxyl groups, which excludes water as well as alkanols, because TFA anhydride, a preferred reactant, will react with hydroxyls. Depending upon the solvent and the proportion either a solution or suspension/solution will be formed. In the latter case the blocking agent goes into solution as it reacts. Examples of suitable solvents are anhydrous benzene, hexane, dioxane, and tetrahydrofuran. A proportion of about 30 percent, by weight, phenethylamine is convenient.

Room temperature (20°–25° C) is also convenient although temperatures from the freezing to the boiling points of the solution could be used, for example form −10 to 45° C.

The blocking agent, preferably TFA anhydride, is added as a solid to the phenethylamine solution or solution/suspension, and the mixture is stirred to the completion of the reaction. Unreacted TFA anhydride is undesirable and the mixture can be refluxed, if necessary, but stirring for up to one hour, without cooling, is normally sufficient; equally, up to 10 percent molar excess of phenethylamine can be useful in avoiding unreacted TFA anhydride.

The TFA - phenethylamine produced is recovered by recrystallization from a solvent such as an acetone/ether system, after removal of the reaction medium solvent by evaporation under reduced pressure.

If trichlorotrifluoro acetone is used as a blocking agent the just described conditions can be employed. As an alternative, ethylthiotrifluoroacetate can be used in aqueous medium, which may be desirable, since it does not react with water and is sparingly soluble in it. A suspension will normally be desirable.

As indicated, if aliphatic hydroxyls are present at $R'''$ or $R''''$, these will also be blocked and a correspondingly higher molar proportion of blocking agent should be used. The position with aromatic hydroxyls is however different. Although if they are present, Reaction Sequence C is preferable, it is appropriate to discuss them under the present heading.

Depending upon the particular conditions, aromatic hydoxyls may not be blocked, especially under neutral to acid conditions. To keep them free, it is desirable to control the pH of the system to from 6 to 8 with dilute HCl if the reaction medium is aqueous. Alternatively, they may be liberated subsequently by treatment with HCl at a pH of from 1 to 3, which can be useful if the reaction medium is non-aqueous. If aromatic hydroxyls are not present, pH control is not normally necessary.

Nitration.

This is generally a standard organic chemistry nitration of a phenyl ring. Some practical details will be mentioned however, as exemplary, to demonstrate the reaction.

The temperature is controlled throughout the nitration to lie between $-10°$ C and $10°$ C to reduce the vigor of the reaction. From 1 to 30 percent, by weight, and preferably around 20 percent of the TFA - phenethylamine product of the previous step is dissolved in concentrated sulfuric acid and up to 20 percent molar excess of fuming nitric acid is added, dropwise, maintaining the temperature at from $-10°$ to $0°$ C. The mixture is stirred for from 30 minutes to 4 hours to complete the reaction. It is then allowed to come to room temperature, which may complete the reaction if the stirring was inadequate, and poured onto an ice/water mixture to precipitate the reaction product, nitro-TFA-phenethylamine. This is filtered off and preferably recrystallized for which acetone/ether can be used. Normally, for specificity of the antibody, a single isomer will be desired and, accordingly, fractional crystallization may be necessary to separate the ortho, meta, and para isomers. Surprisingly, however, it has been found that the reaction can proceed selectively producing substantially only the preferred para isomer. When an isomeric mixture is produced, the separation can, if desired, be made after the next, reduction step.

Reduction.

This, too, is generally a standard organic chemistry reduction or hydrogenation of a nitrophenyl to the amine, and any known procedure can be used provided, of course, that the phenyl ring is not hydrogenated, as well. Some possible practical details will however be described, as exemplary, to demonstrate the step.

From 1 to 10, and preferably about 4 percent, by weight, of the nitro-TFA-phenethylamine from the preceding step is dissolved in ethanol and a palladium/carbon catalyst is added. The mixture is then shaken at room temperature under from 1 to 5, and preferably about 2, atmospheres gauge of hydrogen. This is continued to completion as indicated by measurement of the quantity of hydrogen absorbed. Also, the solution clarifies from an initially yellowish color as the reaction proceeds.

The catalyst is filtered off, the solvent evaporated and the amino-TFA-phenethylamine recovered by recrystallization from an ether/petroleum ether solvent. The product can be fractionally crystallized if necessary.

Diazotization.

The conditions for this step are described, more fully, under Reaction Sequence C. Here, they are similar, and reacting the amino-TFA-phenethylamine is equivalent to the PABA of Reaction Sequence C and the aryl-containing protein is equivalent to the TFA-blocked phenethylamine of Reaction Sequence C.

Purification and Separation.

The product of coupling is conveniently dialyzed to remove small molecule materials. Using an alkaline dialysis solution has the valuable advantage of simultaneously unblocking the original amine group and of removing the blocking group from the dialysate. A pH of from 10 to 12, preferably about 11.5, will generally be necessary and a suitable solution is 0.5 percent sodium carbonate. Six days of dialysis is usually sufficient but from 4 to 10 days may be useful. High purity is desirable.

Desirably the product is then dialyzed for a similar period with a phosphate buffer to reduce the pH to a physiologically compatible level of from 7.4 to 7.6 An injectable solution can then be obtained that can be used directly for raising antibodies. Alternatively, the solution can be lyophilized to recover the solid carrier-diazo-phenethylamine synthetic antigen conjugate.

Exemplary conditions for Reaction Sequence B

The initial blocking of the phenethylamine and the subsequent unblocking and purification of the antigenic conjugate can be similar to what is described for Reaction Sequence A.

Acylation.

This is a standard Friedel Crafts reaction, and the conditions and reagents known to be effective in that reaction can be employed. An example, using succinic anhydride effects the reaction with aluminum chloride in dichloromethane, refluxing and precipitation of the product with water.

The acylated phenethylamine is preferably purified by recrystallization from an ethanol/ether solution. Coupling to a carrier is as described.

Exemplary conditions for Reaction Sequence C

The initial blocking of the phenethylamine and the subsequent unblocking and purification of the antigenic conjugate can be similar to the steps described for Reaction Sequence A.

Diazotization.

This is a standard reaction and the conditions and reagents known to be effective can be employed. However, some exemplary conditions will be described. In this reaction a primary aromatic amine is diazotized into the phenethylamine. For the purposes of description, reference will be made to p-aminobenzoic acid (PABA), it being understood that other compounds can also be used, as described above.

Two aqueous solutions are prepared at 0°–5° C. One is a solution of PABA acidified with HCl to a pH of from 0.5 to 2.0, preferably from 1.0 to 1.5. The concentration is dictated by convenience and solubility, being from about 0.1 to 10 percent by weight, PABA, with approximately 4 percent being preferred. The other solution is a simple, aqueous solution of sodium nitrite which, for example, can be a 1 percent solution.

At a temperature of from 0° to 5° C, the sodium nitrite solution is added, dropwise, to the PABA solution, to an end point with potassium iodide-starch paper. Excess nitrous acid is decomposed with sulfamic acid. Under the acid conditions, the diazonium compound forms the salts.

Hapten coupling.

TFA-blocked phenethylamine is dissolved at about 0.1 weight percent in an aqueous medium at a pH adjusted to be from 9 to 11 with sodium hydroxide. The diazonium solution from the previous step is added, dropwise to this TFA-phenethylamine solution at a temperature maintained at from 0° to 5° C, maintaining also the pH at from 9 to 11 with sodium hydroxide. The mixture is stirred to completion of the reaction which takes from about 20 minutes to 1 hour.

The product is the precipitated and separated. This can be accomplished by adjusting the pH to a neutral point, for example, 7 to 7.5 with HCl, refrigerating for up to 24 hours, and filtering the precipitate. The material can then be fractionated on a silica gel column, using an organic solvent mixture. The desired fractions can be collected with an alcoholic solvent mixture and the solvent evaporated to give the desired product, TFA-ethylamine-azobenzoic acid.

Coupling to a Carrier

In this step a carrier amine group becomes combined with the PABA carboxyl to form an amide bond. In simple solution, the carrier and PABA merely undergo some ionization to the corresponding substituted ammonium salt. Accordingly, to form the amide, the carboxyl group must be activated to remove its tendency to ionize, and this can be done by substituting the hydroxyl hydrogen. In order to proceed to the amide, the substituted PABA intermediate must be of moderate stability, certainly less stable than the amide.

One suitable and preferred acid-activating reactant is a carbodiimide. This is known to be effective and is thought to form a pseudourea intermediate. Other include isobutylchloroformate and thionyl halides. This step of the process will be further described with reference to a carbodiimide, it being understood that other acid-activating reactants can be used.

The carrier is dissolved in water or aqueous methanol or ethanol, depending upon its solubility as known in the art. The concentration is not critical, depending at the lower end of the possible range upon practical operating convenience and at the upper upon the solubility of the carrier. A likely range is from about 1 to about 50 weight percent of carrier to solution, with around 10 weight percent being convenient. The solution is acidified with HCl to a pH of not less than about 3, preferably from 3.9 to 4.1.

The PABA product is dissolved in water or alcohol. Since its solubility is moderate, an excess can be used in suspension. The excess is taken up as the dissolved PABA product reacts; however, too great an excess is not desired so that a practical limit is about 15 weight percent PABA product to solvent. Convenience dictates a lower limit of about 0.5 weight percent PABA product and a preferred range of from 1 to 10 weight percent.

These two solutions, one of which may be a suspension, are mixed and carbodiimide is added as a solid. Preferably, there is a slight stoichiometric excess of carbodiimide over PABA product to maximize material usage.

The reaction mixture is then stirred for from 6 to 8 hours. The stirring can be continued longer, but 8 hours is normally sufficient for the reaction to go to completion. Some reaction should occur after about 1 hour.

In this step the temperature range is desirably from 4° to 25° C., but can go beyond these limits provided that it is not below about $-10°$ C., in which case the solution might freeze, or above a temperature at which substantial decomposition of the carrier occurs. With a proteinic carrier, severe denaturing is likely to occur at about 60° C.

The antigenic conjugate is then purified by dialysis as indicated previously with regard to Reaction Sequence A.

Production of Antibodies and Their Use in Assays

The assay, according to the present invention, is an immunochemical method of assaying for the presence of a target according to the present invention, that target being contained in a sample. The method employs an antibody obtained by the immunologic response of a vertebrate animal to administration of an antigen according to the present invention, and the antibody is specific to the target. Further, the assay employs a standard, the standard and target competitively binding with the antibody to form an antibody-standard complex and an antibody-target complex. The antibody-standard complex has an artificially introduced radiation label so that the complex can be assayed quantitatively by measurement of the radiation emanating from it. In order for the method to be properly employed, the affinities of the antibody for the standard and for the target must be known quantitatively. In employing the method, a known quantity of the sample and a known quantity of the standard are allowed to complete for binding with a known quantity of the antibody. The radiation emanating from the antibody-standard complex so formed is determined so that the quantity of antibody-bound standard can be calculated and the quantity of target in the sample can be deduced. This deduction is carried out by attributing any difference between the quantity of bound standard determined and the quantity expected, based on the known binding characteristics of the antibody, to binding of the antibody with the target.

In an embodiment of the assaying procedure, the introduced label is radioactive and the antibody-standard is separated from any non-complexed, labeled material after allowing competition binding and before determination of the radiation emanated.

In another embodiment of the assaying method, the introduced label is fluorescent and the standard is provided with a chemical moiety giving it a fluorescence spectrum overlapping the natural fluorescence spectrum of the antibody. The complex can then be assayed by measurement of the perturbation of the antibody fluorescence due to binding with the standard.

The standard is a substance known to bind with the antibody and can be, for example, the target, the antigen used to raise the antibody, or the hapten used to make the antigen. Similarly, it can be a similar antigen having the same hapten bound to a different carrier, but as the same position on the hapten. Conveniently, where the radiation constitutes radioactive emission, such as beta or gamma rays, the standard can carry the radioactive label in the form of a radioactive isotope, e.g., tritium, $I^{125}$, or $C^{14}$, although, as an alternative, the antibody can be labeled.

When separation of the complex from the unreacted standard is necessary, as is normally the case with radioactive labeling, this can be effected by phase separation, insolubilizing of one of the components to be separated, etc. Thus, with a labeled antibody, the use of an antigenic standard having a plurality of antibody binding sites causes the antibody-standard complex to precipitate while, if the target is a small molecule, the antibody-target complex will remain in solution. Alternatively, the antibody can be insolubilized, as described elsewhere in the specification, and the standard labeled, so that unreacted standard stays in solution and can easily be separated from the complex.

One example of such a separation is the addition of saturated ammonium sulfate to the complexed mixture. The mixture, with the added ammonium sulfate, is then centrifuged which results in deposition of most of the protein, including the antibody-standard complex. The antibody-standard complex can then be removed as a solid and measurement carried out on this solid. Alternatively, the uncomplexed liquid standard is subjected to measurement or radiation emanation.

A further possibility is to absorb the standard with dextran-charcoal, after allowing for competition binding, and to then make the scintillation count for radiation on the liquid phase containing the antibody-standard complex following separation of the solid phase which contains the unreacted standard. In this case, the standard is labeled and is a small molecule, especially a radioactive isotope labeled target molecule.

While the count for radiation is normally made upon the antibody-standard complex, as this is either more convenient or is believed to reduce experimental error, it will be clear that where there is a separation of unbound, labeled material from the antibody-standard complex, the determination of the radiation emanating from the antibody-standard complex can equally well be made by measuring the radiation emanating from the unreacted, labeled material. From this measurement, the difference from the known amount of labeled material added can be calculated.

The term "radiation" is used in an ordinary dictionary sense and refers to energetic emissions originating from individual atoms or molecules which are generally attributed to internal changes within the atom or molecule. These emissions are in contrast to physical phenomena, such as, for example, precipitations which are the result of the inter-molecular or inter-atomic effects, and may require a large-scale cooperation of a great number of atoms or molecules to be meaningfully expressed. Radiation is significant for immunoassays as it provides a means of remotely monitoring the behavior of very small quantities of matter.

Thus, in addition to energetic emissions, radiation includes such phenomena as fluorescence and electron spin resonance. Fluorescence usually requires excitation by exposure to ultraviolet light, but the product is radiation. Thus, energy, usually in the form of light, is emitted as a result of intra-molecular change.

Where fluorescence is the form of radiation measured, it is feasible for the assay to be conducted without any separation of materials. Thus, antibodies, which are naturally fluorescent, have an absorption spectrum and an emission spectrum. If the standard chosen is a molecule having, as a label, a chemical group which fluoresces in spectra overlapping the antibody, then, when the standard complexes with the antibody, the natural fluorescence of the antibody is perturbed by that of the standard, and this perturbation can be measured. When the emission spectrum of the standard overlaps the absorption spectrum of the antibody, fluorescence enhancement will be observed from the complex at the antibody emission wavelength, and when the absorption spectrum of the standard overlaps the emission spectrum of the antibody, fluorescence quenching will be observed from the complex at the antibody emission wavelength. Comparable effects can be displayed using polarization perturbation.

Electron spin resonance labeled assays can also be conducted without the need for separation. A paramagnetic labeling group, such as a nitroxide ring, is attached, for example, to the standard. When subjected to a microwave frequency magnetic field, an electron spin resonance spectrometer can detect distinct resonance peaks characteristic of the nitroxide ring label. When the standard combines with antibody, these peaks are substantially extinguished, providing a direct indication of the degree of binding.

In most cases, the target in an assay will be the hapten used in making the antigen. However, in some cases, the target may be different. For example, when assaying for a dihydroxyphenethylamine, i.e., a catecholamine, antibody raised to an antigen made by conjugating the equivalent monohydroxy compound can be used, provided that the point of coupling to the monohydroxy hapten is the point of substitution of the second hydroxyl in the target compound. For example, an antigen in which norphenylephrine is coupled through the para position can be ued to raise antibody useful for assaying for norepinephrine. Such an antibody can, of course, be expected, also, to recognize norphenylephrine, itself, and, perhaps, other derivatives of norphenylephrine in which a small substituent is present in the para position. The acceptability of such a result must be based upon the clinical situation which will determine whether it is necessary to distinguish between these targets or whether more than one of the targets are likely to be present in the samples to be analyzed.

In order that those skilled in the art may be better enabled to practice the present invention, the following examples are given. These should be considered as exemplary, only, and not as limiting in any way the full scope of the invention as covered in the appended claims.

EXAMPLE I

Reaction Sequence A a. Preparation of N-Trifuoroacetylamphetamine

A solution of 6.7 gm. of d-amphetamine in 25 ml. of anhydrous benzene is cooled 0° C. To it is added, dropwise, 11 gm. of trifluoroacetic anhydride. The reaction mixture is stirred for one hour, without cooling, and then refluxed for 3 hours. It is allowed to cool and the solvent is removed under reduced pressure. Trituration of the residual oil with ether induces crystallization. Recrystallizaton from acetone ether yields pure N-trifluoroacetylamphetamine with a melting point of 82°–83° C.

b. Preparation of N-Trifluoroacetyl-p-nitroamphetamine

To a cold (−10° to 0 C.) solution of 2.5 gm. of N-TFA-amphetamine in 12.5 ml. of concentrated sulfuric acid is added 0.6 ml. of fuming nitric acid over a period of 15 minutes. The reaction mixture is then stirred for 45 minutes, while maintaining the temperature at −10° to 0° C. It is allowed to warm, gradually, to room temperature over 15 to 20 minutes and is then poured into 100 ml. of ice-water slurry. The precipitate of N-TFA-p-nitroamphetamine is filtered. Recrystallization from acetone-ether give pure N-TFA-p-nitroamphetamine, with a melting point of 146°–147° C.

c. Preparation of N-Trifuoroacetyl-p-aminoamphetamine

A solution of 1 gm. of N-TFA-p-nitroamphetamine in 25 ml. of ethanol is hydrogenated at 30 psig and room temperature (20°–25° C) using 100 mg. Pd/C as a catalyst. The hydrogenation solution is filtered to remove catalyst and the solvent is removed on a rotary evaporator. The residual oil is recrystallized from ether-petroleum ether to give N-TFA-p-aminoamphetamine, with a melting point of 65°–67° C.

d. Coupling of N-TFA-p-aminoamphetamine to BSA 50 mg. of N-TFA-p-aminoamphetamine is dissolved in 1 ml. of 1 N HCl and the solution is cooled to 0°–5° C. To the solution is added a cold (0°–5° C) solution of sodium nitrite (15mg.) in 0.5 ml. water to an end point with starch-iodide paper. Excess nitrous acid is decomposed with a few crystals of sulfamic acid. The cold diazonium salt solution is added dropwise to a cold (0°–5° C) solution of 600 mg. BSA in 10 ml. water which has previously been adjusted to pH 10.5 with 2N sodium hydroxide. During the addition the pH is maintained between 9 and 11 with 2N sodium hydroxide and the temperature is maintained at 0°–5° C. After the addition is complete, the solution is stirred at 0°–5° C for 1 hour at pH 10.5. It is transferred to dialysis tubing and is dialyzed against 6L of 0.5% sodium carbonate for 6 days with daily changes of the sodium carbonate solution. It is next dialyzed against 6L of pH 7.4–7.6 sodium phosphate buffer for four days with daily changes of the buffer solution. The optical density at 280 nm. was determined to be 1.4 for 0.1% solution.

EXAMPLE 2

Reaction Sequence B a. Synthesis of p-succinyl - N-TFA-amphetamine

The N-TFA-amphetamine is prepared as previously described in Example 1a. Into a three-necked flask fitted with a mechanical stirrer and an efficient condenser is put 2.3 gm. of N-TFA-amphetamine, 1.0 gm. of succinic anhydride and 20 ml. of dichloromethane. The solution is cooled to about 10° C and to it is added, in portions, 3 gm of anhydrous aluminum chloride. The reaction mixture is well stirred after each addition. After the additions are complete, the mixture is allowed to reflux with stirring for 15 hours. It is decomposed with 25 ml. of ice water and 1 ml. of concentrated HCl is added. The reaction product separates as an amorphous material, insoluble in both the organic and aqueous layers. It is separated by filtration and the residue is washed with a 5% sodium bicarbonate solution (20 ml.) and then with water. The crude product is crystallized from ethanol ether. Several crystallizations give a pure material with a melting point of 168°–169° C.

b. Coupling of p-succinyl - N-TFA-amphetamine to thyroglobulin 10 mg. of p-succinyl - N-TFA-amphetamine is dissolved in 5 ml. of water adjusted to a pH of 11 with 2N sodium hydroxide. To the solution is added 100 mg. of thyroglobulin and the pH is lowered to about 3.9–4.1. To the mixture is added 15 mg. of soluble carbodiimide, and the mixture is stirred at room temperature for 6 hours. The pH is then readjusted to 12, the solution transferred to dialysis tubing and is dialyzed against 6L of 0.5% sodium carbonate solution to which has been added sufficient 2N sodium hydroxide to raise the pH to 12. The dialysis solution is changed after two days and dialysis continued for a further 2 days. It is then dialyzed against 0.1M phosphate buffer at pH 7.5.

EXAMPLE 3

Reaction Sequence C a. Blocking of Norphenylephrine

Trifluoroacetic anhydride is added, gradually, to a solution of norphenylephrine in anhydrous benzene. It is stirred at room temperature for 24 hours. A quantity of 25 ml. of water is then added to decompose excess acetic anhydride and the solution is stirred for about 1 hour. The solution is transferred to a separatory funnel, the aqueous layer is separated, and the solution is extracted twice with 0.1N HCl. It is then extracted with water. All aqueous phases are discarded and the organic layer is dried, filtered and evaporated to give an oil which is shown to be alpha-N-trifluoroacetylaminomethyl-m-hydroxy-benzyl alcohol-trifluoroacetate ester.

b. Preparation and Purification of Azo-norphenylephrine

Ethyl-p-aminobenzoate is dissolved in aqueous hydrochloric acid and is cooled to between 0° and 5° C. in an ice/water bath. Cold sodium nitrate solution is added, dropwise, to the amine hydrocloride solution to a end point with potassium iodide-starch paper. The temperature of the amine hydrochloride solution is not allowed to rise about 5° C. during the addition of the sodium nitrite.

The ester from Example 3a is dissolved in a minimum amount of 1N sodium hydroxide solution and the pH is then adjusted to between 9 and 10. The alkaline solution is cooled in an ice water bath and the cold diazonium salt is added, dropwise. The temperature is maintained between 0° and 5° C and the pH at between 9 and 10. Upon completion of addition of the diazonium salt, the mixture is stirred for 1 hour at 0° to 5° C and the pH is then adjusted to between 7 and 7.5 with dilute hydrochloric acid. The mixture is placed in a refrigerator overnight.

After refrigeration, the precipitate is filtered and passed down a silica gel column using, as a solvent mixture, 50 parts benzene, 50 parts methanol, and one part acetone alcohol. Fractions are collected and those having an rf. value of 0.5 on the TLC using, as solvent, 25 ml. methanol and 0.1 ml. acetone alcohol are collected. The solvent is evaporated to dryness, yielding the desired product. Coupling of this material to a protein, and unblocking of the hapten is then effected in the manner set forth in Example 2b.

Raising of Antibodies

Approximately 2 mg. doses of the antigen of Example I in 0.1% aqueous solution with Fruend's adjuvant are injected at multiple, subcutaneous sites in rabbits. The injections are repeated at intervals according to known immunization procedure. The rabbits are bled at intervals and the active serum is collected and used without purification.

Radioimmune Assay for Amphetamine

The radioimmune assay is performed by incubating various dilutions of antisera obtained from animal bleedings, with $^3$H-d-amphetamine sulfate (New England Nuclear 6.2 Ce/mM, 137 picograms) in the presence of buffer at 4° C. After 2 hours a neutral, saturated ammonium sulfate solution is added. The resultant precipitates are sedimented by centrifugation at 3,000 rpm for 15 minutes at 4° and the supernates are decanted off. Aliquots of 0.5 ml. of the supernates are added to counting vials, together with 0.5 ml. water and 10 ml. aquasol and counted for tritium. The addition of increasing amounts of unlabeled d-amphetamine to a fixed amount of $^3$H-d-amphetamine and antiserum results in a competitive inhibition of the $^3$H-d-amphetamine bound to antibody.

The relationship of the amount of unlabeled amphetamine added to the inhibition of binding is shown in the table below:

| Picograms of Unlabeled Amphetamine | Percent Inhibition of Binding $^3$H-d-amphetamine |
|---|---|
| 0 | 0 |
| 250 | 12 |
| 500 | 22 |
| 1,000 | 33.5 |
| 10,000 | 83.0 |

Cross reactivity of the antiserum to other amphetamine derivatives are tabulated in the table below:

| Compound | Percent Cross-Reactivity |
|---|---|
| d-amphetamine | 100 |
| l-amphetamine | 1.45 |
| methadrine | 0.45 |
| metanephrine | <0.0125 |
| normetanephrine | <0.0125 |
| tyramine | 3.4 |

The cross-reactivity is defined according to the method of Abraham as the relative quantity of subject compound to cross-reactant that produces 50% inhibition, multiplied by 100 for percentage.

The material produced according to Example 2b was also tested to show the relationship of unlabeled amphetamine added to the inhibition of binding and/or cross-reactivity of the antiserum to other amphetamine derivatives. The relationship of the amount of amphetamine added to the inhibition of binding is shown in the table below:

| Picograms of Unlabeled Amphetamine | Percent Inhibition of Binding $^3$H-d-amphetamine |
|---|---|
| 0 | 0 |
| 10 | 13 |
| 100 | 27 |
| 1,000 | 37 |
| 10,000 | 65 |

The cross-reactivity of the antiserum is shown in the following table:

| Compound | Percent Cross-Reactivity |
|---|---|
| d-amphetamine | 100 |
| l-amphetamine | 3.8 |
| methadrine | 3.3 |

If desired, the antibodies of this invention can be insolubilized, or otherwise supported, on a solid matrix. Examples of materials to which the antibody can be attached are glass, synthetic polymers, synthetic resins, and cellulose. The material to which the antibody is attached or otherwise insolubilized can have an extensive, continuous form, such as a sheet, or it can be in the form of discrete particles of desired size. The antibody can be secured to the material in a number of ways.

Among the methods for attaching or otherwise insolubilizing the antibody to a solid matrix are covalent bonding, van der Waal's forces, hydrogen boding, etc. Thus, the methods for attaching the antibody to the solid matrix are relatively weak intermolecular forces, covalent bonds, or the adsorptive forces attributable to a porous surface. An example of van der Waal's forces occurs with the adhesion of an antibody to a predominantly hydrophobic plastic surface, such as a polyolefin. Apparently, there is hydrophobic bonding to the hydrophobic amino acid residues of the antibody.

Some of the methods for bonding of the antibody to a solid matrix are discussed in Weliky and Weetall, *Immunochemistry*, Vol. 2, pages 293–322 (1965).

Another method for conveniently covalently bonding the antibody to a solid is by diazotizing available amino groups on the antibody into available, activated, aromatic rings on the solid material.

It may be desirable to modify the material, particularly for the purpose of securing the antibody to it. Thus, for covalent bonding, carbodiimide condensation, with the formation of an amide bond between the antibody and the material, can be used. For this purpose, the material should have available primary, non-aromatic amine groups or carboxyl groups to couple with, respectively, available carboxyl or amino groups on the antibody. An amino glass suitable for this purpose is known. Suitable synthetic resins or polymers may be available, in addition, or existing resins can be modified. Similarly, many derivatized celluloses are known, and cellulose can, in general, be provided with appropriate groups.

In attaching the antibody to the substrate material, it is normally desirable to ensure that the active binding site of the antibody remains available and accessible. This can be facilitated by blocking the site before coupling to the support material, and unblocking thereafter. Blocking can be conveniently effected by complexing the antibody with the hapten for which it is specific and deblocking can be effected with an eluting agent, for example, acetic acid or urea.

For sorption on a porous surface, another method for insolubilizing the antibody on a solid matrix, it is desirable for the pore size of the material, e.g., porous particles, to be selected for optimum accommodation of the antibody.

Although specific examples and specific procedures according to the present invention have been illustrated, these are not to be considered as limiting in any way, the appended claims.

What is claimed is:

1. A synthetic antigen of formula:

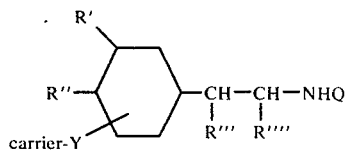

where R' and R'' of the phenethylamine hapten are individually selected from the class consisting of —H, —OH, and —OCH$_3$, where when either R' or R'' is —OCH$_3$ the other is —OH; R''' of the phenethylamine hapten is selected from the class consisting of —H and —OH; R'''' of the phenethylamine hapten is selected from the class consisting of —H, —OCH$_3$, and —C$_2$H$_5$; Q of the phenethylamine hapten is selected from the class consisting of —H and —CH$_3$; Y is a linking group which is the residue of the reaction of a coupling agent with a reactive group derivatized into the phenol ring and of the coupling agent with the carrier; and the carrier is a macromolecule conferring antigenicity.

2. The synthetic antigen of claim 1 wherein Y is diazo and R' and R'' are both —H.

3. The synthetic antigen of claim 1 in which Y is a dicarboxylic acid residue.

4. The synthetic antigen of claim 1 wherein Y includes a phenazo group bonded to the phenethylamine ring and the phenethylamine includes an aromatic hydroxyl.

5. Protein-p-diazoamphetamine.
6. Protein-p-succinylamphetamine.
7. Protein-p-benzoyldiazo-m-epinephrine.
8. Protein-p-benzoyldiazo-p-norphenylephrine
9. Antibody raised by the antigen of claim 1 and specific to the phenethylamine hapten.
10. Antibody raised by the antigen of claim 5 and specific to the amphetamine.
11. Antibody raised by the antigen of claim 6 and specific to amphetamine.
12. Antibody raised by the antigen of claim 7 and specific to the epinephrine.
13. Antibody raised by the antigen of claim 8 and specific to norphenylephrine.
14. The antibody of claim 9 insolubilized by securing it to a solid matrix.

15. The antibody of claim 10 insolubilized by securing it to a solid matrix.
16. The antibody of claim 11 insolubilized by securing it to a solid matrix.
17. The antibody of claim 12 insolubilized by securing it to a solid matrix.
18. The antibody of claim 13 insolubilized by securing it to a solid matrix.
19. An immunochemical method for assaying for the presence of an antigen target in a sample, said antigen having the formula:

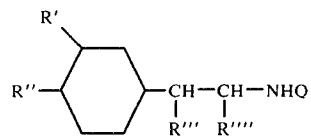

where R' and R'' are individually selected from the class consisting of —H, —OH, and —OCH$_3$, where when either R' and R'' is —OCH$_3$ the other is —OH; R''' is selected from the class consisting of —H and —OH; R'''' is selected from the class consisting of —H, —OCH$_3$, and —C$_2$H$_5$; Q is selected from the class consisting of —H and —CH$_3$; wherein said method employs an antibody obtained by the immunologic response of a vertebrate animal to administration of an antigen according to claim 1 and wherein said antibody is specific to the target, said method also employing a standard, the antibody binding with the target to form an antibody-target complex and competitively binding with the standard to form an antibody-standard complex, the antibodystandard complex having an artificially introduced radiation label enabling the complex to be assayed quantitatively by measurement of radiation emanating from it, the affinities of the antibody for the standard and for the target being known quantitatively, said method comprising allowing a known quantity of the sample and a known quantity of the standard to compete for binding with a known quantity of the antibody and determining the radiation emanating from the antibody-standard complex, thereby enabling the quantity of antibody-bound standard to be calculated and the quantity of target in the sample to be deduced.

20. The method of claim 19 wherein the label is radioactive and the antibody-standard complex is separated from any non-complexed labeled material after allowing competition binding and before determination of the emanated radiation.

21. The method of claim 19 wherein the label is fluorescent and the standard is provided with a chemical moiety giving it a fluorescence spectrum overlapping the natural fluorescence spectrum of the antibody, whereby the complex can be assayed by measurement of the perturbation of the antibody fluorescence due to its binding with the standard.

* * * * *

UNITED STATES PATENT AND TRADEMARK OFFICE
CERTIFICATE OF CORRECTION

PATENT NO. : 3,996,344
DATED : December 7, 1976
INVENTOR(S) : Stanley J. Gross

It is certified that error appears in the above-identified patent and that said Letters Patent are hereby corrected as shown below:

at Column 2, line 25, "spacific" should read --specific--.

at Column 3, line 24 "R"' " should read --R""--.

at Column 3, lines 11-20 the formula should read as follows:

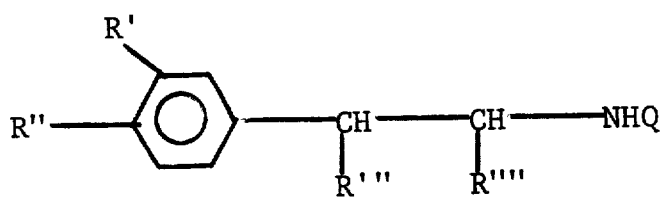

UNITED STATES PATENT AND TRADEMARK OFFICE
CERTIFICATE OF CORRECTION

PATENT NO. : 3,996,344
DATED : December 7, 1976
INVENTOR(S) : Stanley J. Gross

It is certified that error appears in the above-identified patent and that said Letters Patent are hereby corrected as shown below:

at Column 3, lines 29-36 the formula should read as follows:

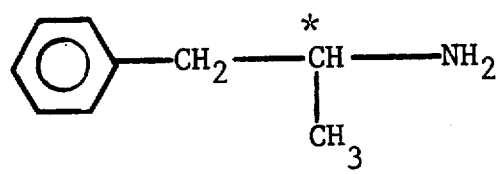

at Column 3, lines 37-45 the formula should read as follows:

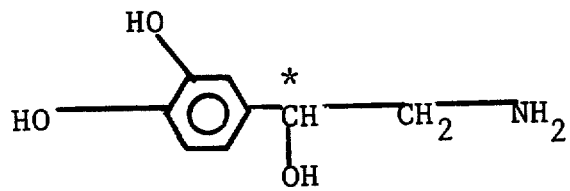

UNITED STATES PATENT AND TRADEMARK OFFICE
CERTIFICATE OF CORRECTION

PATENT NO. : 3,996,344
DATED : December 7, 1976
INVENTOR(S) : Stanley J. Gross

It is certified that error appears in the above-identified patent and that said Letters Patent are hereby corrected as shown below:

at Column 3, lines 46-55 the formula should read as follows:

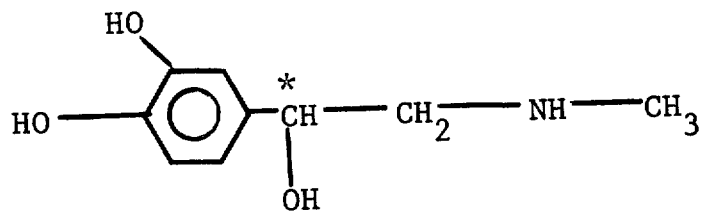

at Column 6, lines 19-25 the formula should read as follows:

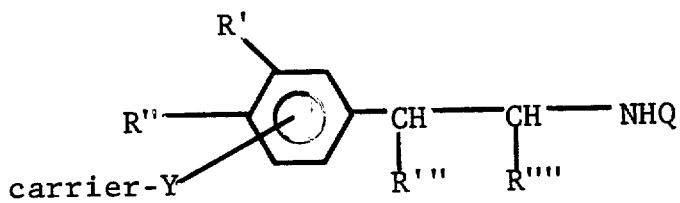

UNITED STATES PATENT AND TRADEMARK OFFICE
CERTIFICATE OF CORRECTION

PATENT NO. : 3,996,344
DATED : December 7, 1976
INVENTOR(S) : Stanley J. Gross

It is certified that error appears in the above—identified patent and that said Letters Patent are hereby corrected as shown below:

at Column 8, lines 57-65 the formula should read as follows:

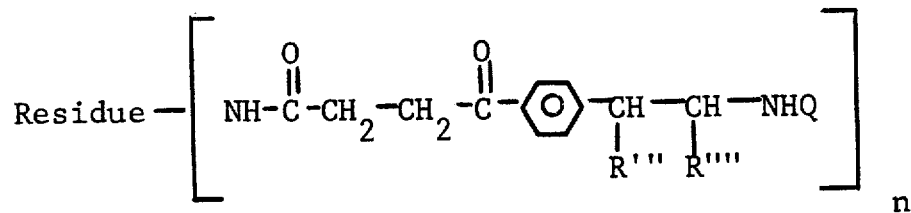

UNITED STATES PATENT AND TRADEMARK OFFICE
CERTIFICATE OF CORRECTION

PATENT NO. : 3,996,344
DATED : December 7, 1976
INVENTOR(S) : Stanley J. Gross

It is certified that error appears in the above-identified patent and that said Letters Patent are hereby corrected as shown below:

at Column 9, lines 15-35 the formula should read as follows:

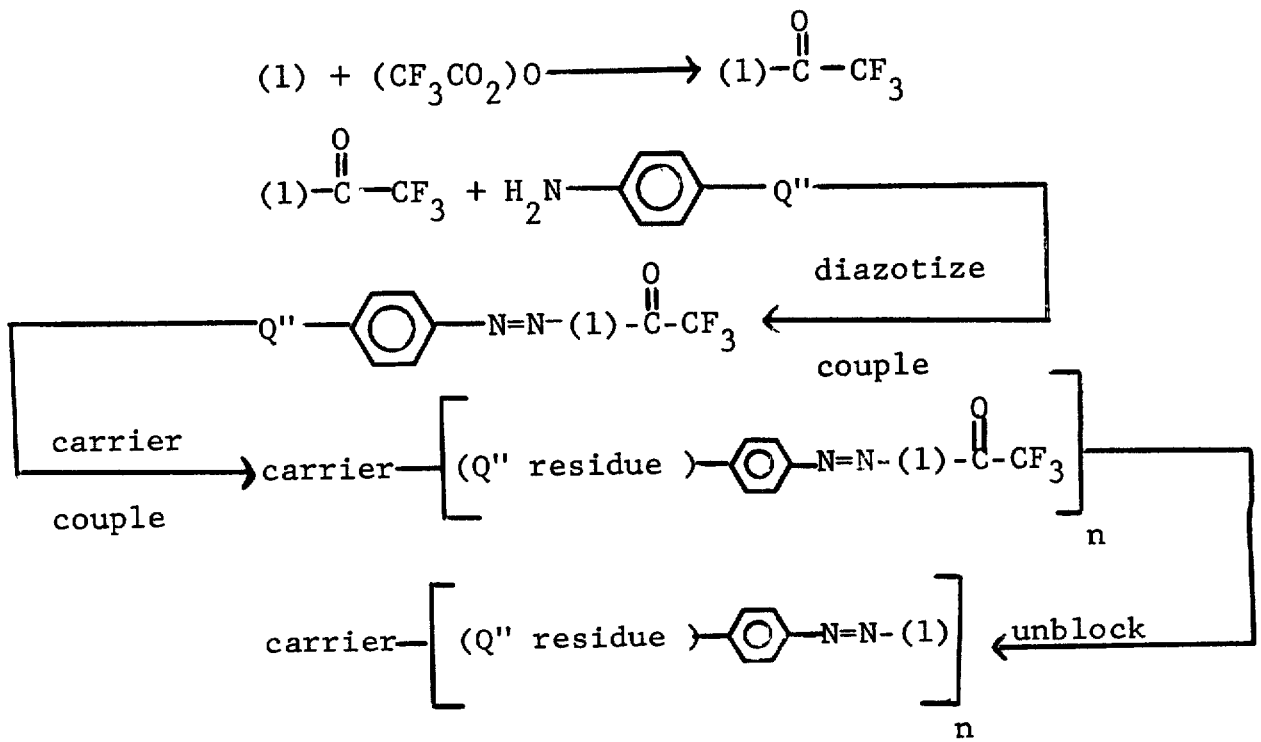

UNITED STATES PATENT AND TRADEMARK OFFICE
CERTIFICATE OF CORRECTION

PATENT NO. : 3,996,344
DATED : December 7, 1976
INVENTOR(S) : Stanley J. Gross

It is certified that error appears in the above-identified patent and that said Letters Patent are hereby corrected as shown below:

at Column 10, line 65 "form" should read --from--.

at Column 15, line 6 "but as the same position" should read --but at the same position--.

at Column 16, line 63 "N-Trifuoroacetylamphetamine" should read --N-Trifluoroacetylamphetamine--.

at Column 17, line 8 "(-10° to 0  C.)" should read --(-10° to 0°C.)--.

at Column 17, line 20 "N-Trifuoroacetyl" should read --N-Trifluoroacetyl--.

at Column 19, line 9 "Fruend's" should read --Freund's--.

at Column 20, line 33 "boding" should read --bonding--.

at Column 20, line 45 "amother" should read --another--.

UNITED STATES PATENT AND TRADEMARK OFFICE
CERTIFICATE OF CORRECTION

PATENT NO. : 3,996,344

DATED : December 7, 1976

INVENTOR(S) : Stanley J. Gross

It is certified that error appears in the above-identified patent and that said Letters Patent are hereby corrected as shown below:

at Column 21, lines 15-22, Claim 1 the formula should read as follows:

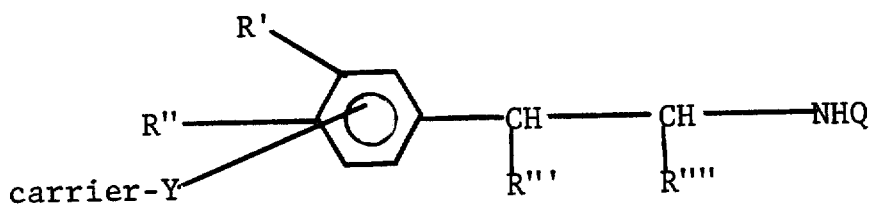

at Column 22, lines 15-22, Claim 19 the formula should read as follows:

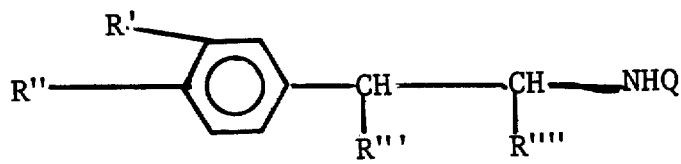

Signed and Sealed this

Twenty-ninth Day of March 1977

[SEAL]

Attest:

RUTH C. MASON
Attesting Officer

C. MARSHALL DANN
Commissioner of Patents and Trademarks